US005812684A

United States Patent [19]

Mark

[11] Patent Number: 5,812,684

[45] Date of Patent: Sep. 22, 1998

[54] PASSENGER COMPARTMENT NOISE ATTENUATION APPARATUS FOR USE IN A MOTOR VEHICLE

[75] Inventor: Joseph Steven Mark, Dearborn, Mich.

[73] Assignee: Ford Global Technologies, Inc., Dearborn, Mich.

[21] Appl. No.: 498,773

[22] Filed: Jul. 5, 1995

[51] Int. Cl.[6] .............................. H04B 1/00; H03B 29/00; A61F 11/06

[52] U.S. Cl. .......................... 381/86; 381/71.4; 381/71.2; 381/152; 296/146.1; 296/146.2

[58] Field of Search ................................ 381/71, 94, 86, 381/152; 296/146.2, 146.9, 149, 145, 146.1, 146.15, 146.16; 415/119

[56] References Cited

U.S. PATENT DOCUMENTS

| | | | |
|---|---|---|---|
| 3,058,015 | 10/1962 | Nesh . | |
| 3,602,331 | 8/1971 | Baschorr . | |
| 4,025,724 | 5/1977 | Davidson, Jr. et al. . | |
| 4,449,235 | 5/1984 | Swigert . | |
| 4,551,849 | 11/1985 | Kasai et al. | 381/152 |
| 4,566,118 | 1/1986 | Chaplin et al. . | |
| 4,589,137 | 5/1986 | Miller . | |
| 4,807,294 | 2/1989 | Iwata et al. | 381/86 |
| 4,927,207 | 5/1990 | Kishino | 296/146.2 |
| 4,947,434 | 8/1990 | Ito . | |
| 5,018,203 | 5/1991 | Sawyers et al. . | |
| 5,106,149 | 4/1992 | Calossop | 296/146.9 |
| 5,170,433 | 12/1992 | Elliott et al. | 381/94 |
| 5,219,037 | 6/1993 | Smith et al. . | |
| 5,270,607 | 12/1993 | Terajima . | |
| 5,315,661 | 5/1994 | Gossman et al. . | |
| 5,355,417 | 10/1994 | Burdisso et al. . | |
| 5,370,340 | 12/1994 | Pla . | |
| 5,371,801 | 12/1994 | Powers et al. . | |
| 5,391,053 | 2/1995 | Pla et al. . | |
| 5,410,607 | 4/1995 | Mason et al. . | |
| 5,473,698 | 12/1995 | Garnjost et al. | 381/86 |
| 5,498,127 | 3/1996 | Kraft et al. | 415/119 |
| 5,546,469 | 8/1996 | Donahoe | 381/152 |
| 5,548,653 | 8/1996 | Pla et al. | 381/71 |
| 5,734,727 | 3/1998 | Flaherty et al. | 381/86 |

OTHER PUBLICATIONS

Dynamic Characteristics of Automotive Front Door Side Glass, Thesis, 1994, Michigan Technological University, pp. 189–190.

*Primary Examiner*—Curtis A. Kuntz
*Assistant Examiner*—Xu Mei
*Attorney, Agent, or Firm*—Gregory P. Brown

[57] ABSTRACT

An noise attenuation system disposed on a movable side glass (14) of a motor vehicle for reducing the noise within the passenger compartment. In the preferred embodiment, a piezoceramic sensor (46) and piezoceramic actuators (42, 44) are disposed on a side glass (14) below the beltline (24) of a door (10) on a motor vehicle. The actuators (42, 44) are controllably vibrated in reverse phase to a signal generated by the sensor (46) to cancel or reduce vibrations of the side glass (14). The noise transmitted into the passenger compartment by the side glass (14) is thereby significantly reduced.

13 Claims, 2 Drawing Sheets

PASSENGER COMPARTMENT NOISE ATTENUATION APPARATUS FOR USE IN A MOTOR VEHICLE

BACKGROUND OF THE INVENTION

1. Field of the Invention

This invention generally relates to a noise attenuation apparatus for use in a motor vehicle. More particularly, the present invention relates to an apparatus for controlling the noise transmitted into a passenger compartment of a motor vehicle through windows of the vehicle.

2. Disclosure Information

For many years motor vehicle manufacturers have pursued continuous improvements in reducing the noise present in the passenger compartment of motor vehicles during operation. At the height of this activity, manufacturers have pursued actively controlling the noise by using a complex array of loudspeakers and sensors distributed within the passenger compartment. Sensors, such as a microphones, measure the noise in the interior of the car. A central processor determines the signal content of the noise and generates an appropriate anti-noise signal. A multi-channel amplifier drives the anti-noise signal throughout the corresponding loudspeakers, thereby effectively canceling the noise. These complex systems are particularly effective for reducing random noise occurring due to the operation of the vehicle, in particular, noises originating from the powertrain.

In seeking less complex and more cost efficient methods of reducing interior noise levels, motor vehicle manufacturers have successfully developed a variety of simple and cost effective ways to reduce the noise level in the passenger compartment. This is particularly true in the luxury segment where customers expect very quiet interior operating noise levels. These reductions in noise are primarily due to improvements in powertrain balance and tolerances, increasingly rigid vehicle structures and sound isolating materials. These simple, low cost solutions have significantly reduced the variety of noises being transmitted into the passenger compartment.

These improvements have reduced the noise levels to the point where customers are now aware of noises previously unrecognized. For instance these noises may be generated by turbulent wind beating on the windows, rain impacting the windows, and noise generated by the tire to road interface which is then transmitted by the windows into the passenger compartment. While these noises could be reduced through the use of an active noise cancellation system as described above, however those systems have been determined to be too complex and costly.

It would be desirable to provide a noise attenuation system capable of reducing noises transmitted through the glass into the passenger compartment of the motor vehicle that is simple and cost efficient.

SUMMARY OF THE INVENTION

The present invention provides a unique noise attenuation apparatus for use in an motor vehicle having a passenger compartment. The noise attenuation apparatus reduces objectionable noise within the passenger compartment thereby improving customer satisfaction.

In the presently preferred embodiment, the noise attenuation apparatus includes a transparent member resiliently supported from a structural component of the motor vehicle. The transparent member has an interior surface exposed to the passenger compartment, and an exterior surface exposed to an exterior surrounding the motor vehicle.

A sensor is provided for sensing vibrations of the transparent member and generating a vibration signal corresponding thereto. A controller generates an attenuation signal corresponding to the vibration signal generated by the sensor. An actuation device displaces the transparent member in response to the attenuation signal so as to reduce noise radiated from the transparent member.

An advantage of this apparatus is the low cost attenuation of noise transmitted into the passenger compartment in a simple and cost efficient manner. One example includes noise transmitted through a side glass that is driven by the wind acting on the exterior of the side glass as the vehicle is operated.

Other objects, features and advantages of the present invention will become apparent to those skilled in the art from the drawings, detailed description and claims which follow.

DETAILED DESCRIPTION OF THE PREFERRED EMBODIMENT

Figure 1:
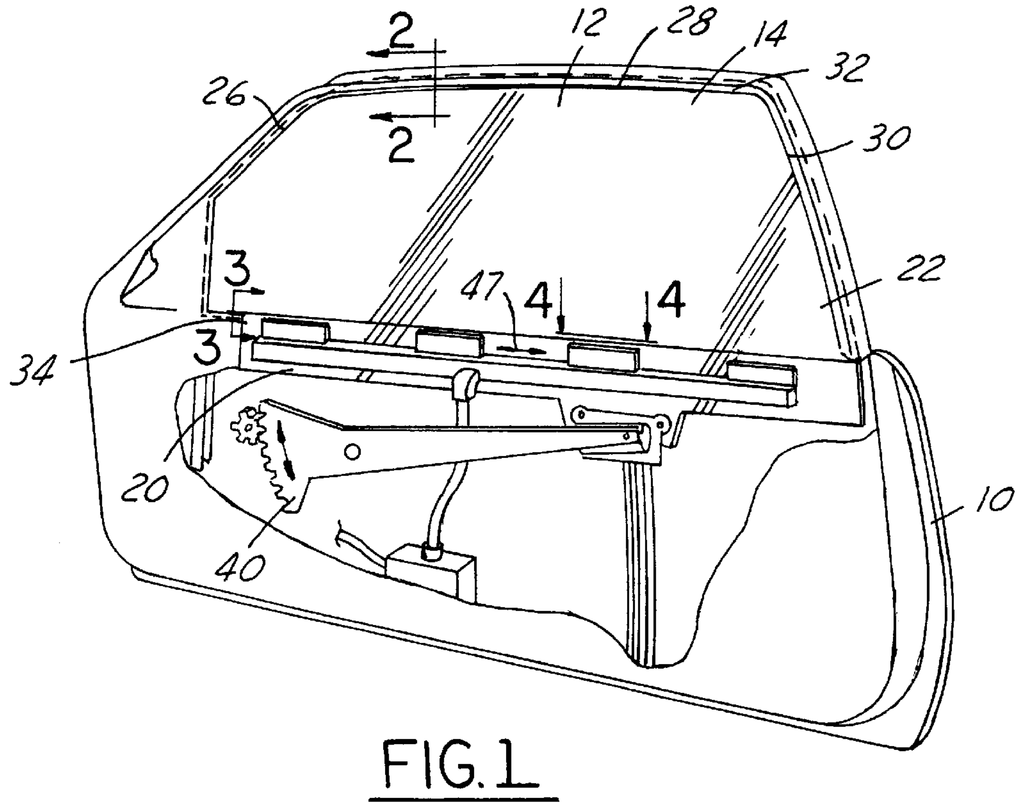
FIG. 1 is a partially cut-away perspective view of a door for a motor vehicle incorporating the preferred embodiment of this invention.
Figure 2:
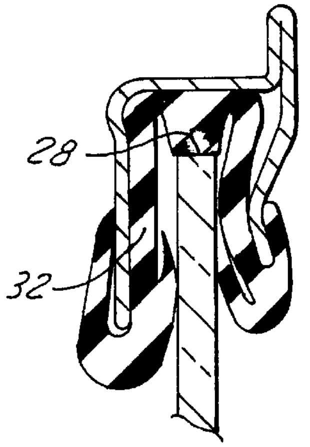
FIG. 2 is a section view illustrating an elastomeric glass run supporting a side glass in the door of FIG. 1.
Figure 3:
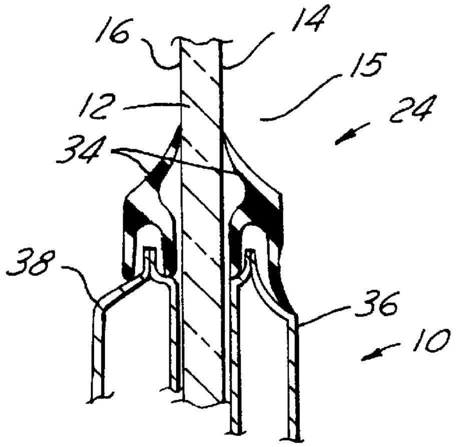
FIG. 3 is a section view illustrating an elastomeric strip disposed on a beltline of the door of FIG. 1.

Referring now to FIGS. 1–3, a structural member, such as a door 10, of a motor vehicle having a transparent member, such as a moveable side glass 12 is shown. The side glass 12 includes an interior surface 14 exposed to a passenger compartment 15 of the motor vehicle and an exterior surface 16 opposite from the interior surface 14 and exposed to an exterior 18 surrounding the motor vehicle. The side glass 12 includes a lower portion 20 and an upper portion 22, the lower portion 20 being characterized in that it is always below a beltline 24 of the door 10. The extent to which the upper portion 22 protrudes above the beltline 24 depends on the vertical positioning of the moveable side glass 10. It should be recognized that the structural component and transparent member may alternatively be a wind shield or a rear window and their associated supporting structural components.

The side glass 12 also includes a forward edge 26, an upper edge 28 and a rearward edge 30, each of which fully engage a elastomeric glass run 32 disposed in the door 10 when the window is in the upper most vertical position. The upper portion 22 of the side glass 12 passes through an elastomeric strip 34 disposed on inner and outer panels 36, 38 of the door 10 at the beltline 24. The door 10 includes a window regulator 40, which can be manually or electrically operated to drive the side glass 12 up and down through the elastomeric strip 34 into engagement with the elastomeric glass run 32.

Figure 4:
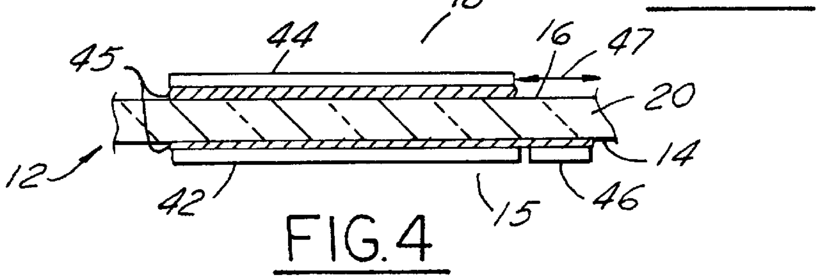
FIG. 4 is a section view illustrating inner and outer piezoceramic actuators and a piezoceramic sensor disposed on a side glass below a beltline of the door according to the present invention.

Referring now to FIG. 4, in the preferred embodiment actuation is provided by inner and outer piezoceramic elements 42, 44 bonded with an adhesive 45 to the interior and exterior surfaces 14, 16, respectively, of the lower portion 20 of the side glass 12. Although mechanical actuators are considered to be a functional alternative, the size, weight, cost and durability of piezoceramic type actuator make them the preferred form of actuator over mechanical alternatives. Additionally, piezoceramic actuators do not require a reaction support to generate an actuation force, as do various mechanical alternatives. This is especially important on moveable side glass, since packaging the reaction support would have to accommodate movement of the glass. The piezoceramic element changes shape when a voltage is applied across the body of the element. When the element is bonded to a surface, the elements change in shape is reacted as a line moment around the edge of the element. The size, thickness, shape and applied voltage determine the magnitude of the moment applied to the side glass.

In the preferred embodiment, four actuator pairs 42, 44 are disposed on the lower portion 20 of the side glass 12 along a line 47 corresponding to an antinode for a fundamental mode of vibration of the side glass. This fundamental mode may be determined analytically, taking into account the rigidity of the side glass 12, the elastomeric glass run 32, the elastomeric strip 34 and the dynamic characteristics of the supporting components of the window regulator 40. Alternatively, this antinode may be determined through conventional laboratory techniques.

In the preferred embodiment, a sensor 46 is bonded to the interior surface 14 of the side glass 12, adjacent to each actuator pair 42, 44. A piezoceramic element may be used as a sensor, since deformation of the piezoceramic generates an electrical charge proportional to the deformation. For simplicity, the piezoceramic sensor may be of the same construction as the piezoceramic actuator. It is desirable to include a sensor 46 for each actuator pair 42, 44 for precise control of vibration at each actuator pair. It should be recognized that the sensor 46 could be disposed on either the interior surface 14 or the exterior surface 16 while providing equivalent functionality and operability.

Figure 5:
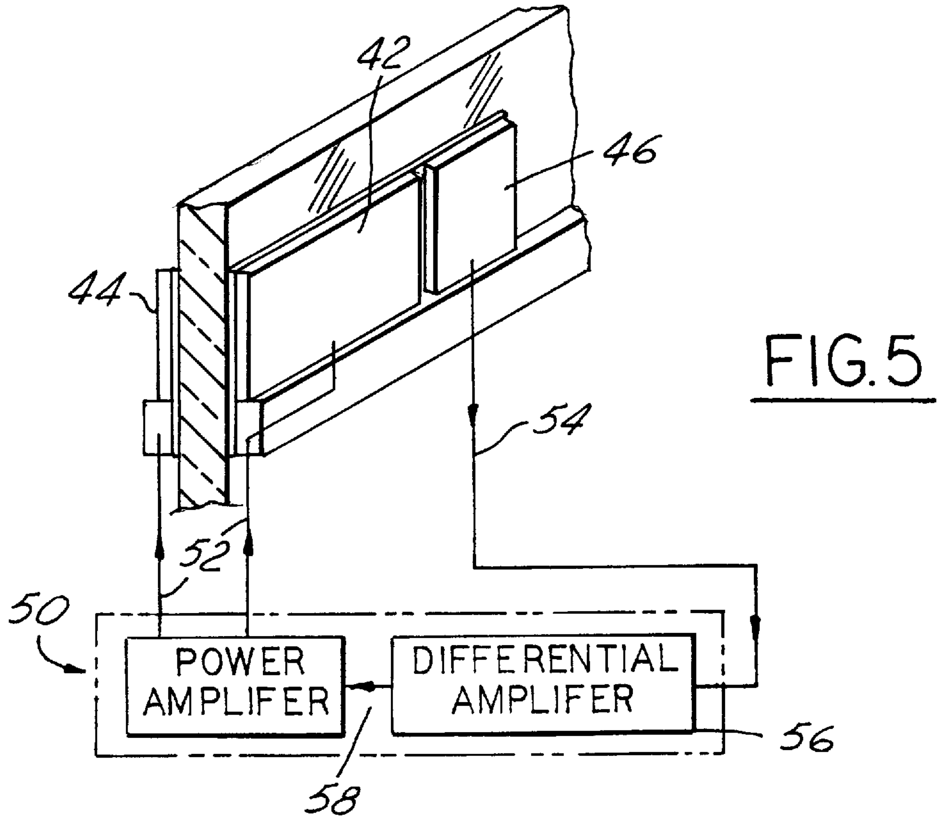
FIG. 5 is a partial schematic view illustrating inner and outer piezoceramic actuators and a piezoceramic sensor connected to a controller according to the present invention.

Referring to FIG. 5, a control device 50 is shown attached to the actuator pair 42, 44 and the associated sensor 46. In the preferred embodiment, a simple integral controller including a differential amplifier 56 produces an output signal 58 proportional to the integral of a vibration signal 54 generated by sensor 46 and having a phase reversed from the phase of the vibration signal 54. The output signal 58 is then amplified by a conventional direct current amplifier generating an attenuation signal 52. An integral controller has been described here as a part of the preferred embodiment, however, the present invention is not so limited. It should be recognized that a variety of control theories may be substituted, such as proportional, derivative and variations thereof without changing the function or operability of the present invention.

Figure 6:
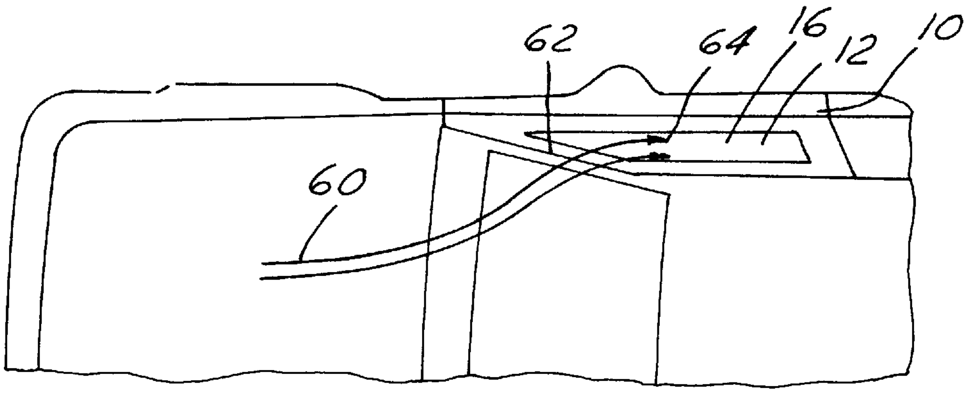
FIG. 6 is a top quarter view of a motor vehicle illustrating air flow along a side glass according to the present invention.

Referring now to FIG. 6, application of the present embodiment will now be described. As the motor vehicle 59 travels through the air, air flows past the various components on the car. As the air passes the exterior surface 16 of the side glass 12 of the door 10, the air flow 60 separates at the forward edge of the door 62 and the flow reattaches at a reattachment point 64 downstream on the side glass 12. The creates a pressure differential along the exterior surface 16 of the side glass 12, which forces the side glass 12 into vibration. Unabated, this vibration increases the noise level in the passenger compartment.

The reattachment of the air flow 60 presents the equivalent of a random forcing function acting on the exterior surface 16 of the side glass 12, which in turn excites the dominant, or fundamental vibratory mode of the side glass 12. To cancel or reduce this vibration, sensor 46 detects this vibration and generates a voltage proportional to the vibration. Controller 50 generates the attenuation signal 52 to drive the actuators 42, 44 to cancel or significantly reduce the vibration of the side glass 12, thereby reducing the noise radiated from the interior surface 14 of the side glass 12 into the passenger compartment.

The foregoing description presents a single embodiment of the present invention. Details of construction have been shown and described for purposes of illustration rather than limitation. Other modifications and alterations of the invention will no doubt occur to those skilled in the art that will come within the scope and spirit of the following claims.

I claim:

1. A noise attenuation apparatus for use in a motor vehicle having a passenger compartment, said noise attenuation apparatus comprising:

a transparent member resiliently supported from a structural component of the motor vehicle, said transparent member having an interior surface exposed to the passenger compartment, and an exterior surface exposed to an exterior surrounding the motor vehicle;

sensor means for sensing vibrations of said transparent member and generating a vibration signal corresponding thereto;

control means for generating an attenuation signal corresponding to said vibration signal;

actuation means for vibrating said transparent member in response to said attenuation signal so as to reduce noise radiated from said transparent member said transparent member is a moveable side glass disposed in a door of the motor vehicle; and said actuator means is disposed on a lower portion of said side glass within said door.

2. A noise attenuation apparatus according to claim 1, wherein said transparent member further comprises:

a moveable side glass disposed in a door of the motor vehicle, said side glass having a lower portion of said glass, and an upper portion of said glass protruding from a beltline of said door;

a window regulator supporting said side glass from said lower portion; and an elastomeric strip attached to said beltline; and an elastomeric glass run resiliently supporting said glass in said door.

3. A noise attenuation apparatus according to claim 2, wherein said actuator means comprises:

a outer piezoceramic actuator disposed on said exterior surface of said lower portion of said door glass; and a inner piezoceramic actuator disposed on said interior surface of said lower portion of said door glass, opposite said outer piezoceramic actuator.

4. A noise attenuation apparatus according to claim 2, wherein said sensor means comprises a piezoceramic panel bonded to said lower portion of said glass adjacent to said actuator means.

5. A noise attenuation apparatus according to claim 2, wherein said actuator means comprises:

a plurality of inner piezoceramic actuators aligned along said interior surface of said lower portion of said glass below said beltline; and a plurality of outer piezoceramic actuators aligned along said exterior surface of said lower portion of said glass below said beltline.

6. A noise attenuation apparatus for use in a motor vehicle having a passenger compartment, said noise attenuation apparatus comprising:

a moveable side glass resiliently supported from within door of the motor vehicle, said side glass having a lower portion of said glass, and an upper portion of said glass protruding above a beltline and an interior surface exposed to the passenger compartment, and an exterior surface exposed to an exterior surrounding the motor vehicle;

sensor means for sensing vibrations of said side glass and generating a vibration signal corresponding thereto;

control means for generating an attenuation signal corresponding to said vibration signal; and actuation means for vibrating said side glass in response to said attenuation signal so as to cancel said vibrations of said side glass thereby reducing noise radiated from said side glass.

7. A noise attenuation apparatus according to claim 6, wherein said side glass further comprises:

a window regulator supporting said side glass from said lower portion; and an elastomeric strip attached to said beltline; and an elastomeric glass run resiliently supporting said glass in said door.

8. A noise attenuation apparatus according to claim 7, wherein said actuator means is disposed on said lower portion of said side glass within said door.

9. A noise attenuation apparatus according to claim 7, wherein said actuator means is disposed on said lower portion of said side glass at a position corresponding to an antinode of said side glass.

10. A noise attenuation apparatus according to claim 8, wherein said actuator means comprises:

an outer piezoceramic actuator disposed on said exterior surface of said lower portion of said door glass; and an inner piezoceramic actuator disposed on said interior surface of said lower portion of said door glass, opposite said outer piezoceramic actuator.

11. A noise attenuation apparatus according to claim 8, wherein said sensor means comprises a piezoceramic sensor panel bonded to said lower portion of said glass adjacent to said actuator means.

12. A noise attenuation apparatus according to claim 8, wherein said actuator means comprises:

a plurality of inner piezoceramic actuators aligned along said interior surface of said lower portion of said glass below said beltline; and a plurality of outer piezoceramic actuators aligned along said exterior surface of said lower portion of said glass below said beltline.

13. A noise attenuation apparatus for use in a motor vehicle having a passenger compartment, said noise attenuation apparatus comprising:

a moveable side glass resiliently supported from within door of the motor vehicle, said side glass having a lower portion of said glass, and an upper portion of said glass protruding above a beltline and an interior surface exposed to the passenger compartment, and an exterior surface exposed to an exterior surrounding the motor vehicle;

a window regulator supporting said side glass from said lower portion; and an elastomeric strip attached to said beltline;

an elastomeric glass run resiliently supporting said glass in said door;

sensor means for sensing vibrations of said side glass and generating a vibration signal corresponding thereto;

control means for generating an attenuation signal corresponding to said vibration signal; and actuation means disposed on said lower portion of said side glass at a position corresponding to an antinode of said side glass, said actuation means being adapted for vibrating said side glass in response to said attenuation signal so as to cancel said vibrations corresponding to said antinode thereby reducing noise radiated from said side glass.

* * * * *